(12) United States Patent
Kamiyama et al.

(10) Patent No.: US 10,556,297 B2
(45) Date of Patent: Feb. 11, 2020

(54) WELDED SECTION EXAMINING DEVICE

(71) Applicant: HONDA MOTOR CO., LTD., Minato-ku, Tokyo (JP)

(72) Inventors: Masahiko Kamiyama, Tochigi-ken (JP); Tetsuya Ozawa, Tochigi-ken (JP); Atsuhiro Hatanaka, Tochigi-ken (JP); Yoshiyuki Izumi, Tochigi-ken (JP)

(73) Assignee: HONDA MOTOR CO., LTD., Tokyo (JP)

(*) Notice: Subject to any disclaimer, the term of this patent is extended or adjusted under 35 U.S.C. 154(b) by 0 days.

(21) Appl. No.: 16/233,227

(22) Filed: Dec. 27, 2018

(65) Prior Publication Data

US 2019/0210158 A1 Jul. 11, 2019

(30) Foreign Application Priority Data

Jan. 10, 2018 (JP) .................. 2018-002220

(51) Int. Cl.
  *B23K 31/12* (2006.01)
  *H02K 15/02* (2006.01)
  *G01N 21/956* (2006.01)
  *G06T 7/00* (2017.01)

(52) U.S. Cl.
  CPC ..... *B23K 31/125* (2013.01); *G01N 21/95607* (2013.01); *G06T 7/001* (2013.01); *H02K 15/024* (2013.01); *G06T 2207/30164* (2013.01)

(58) Field of Classification Search
  CPC ............ B23K 31/125; G01N 21/95607; G06T 7/001; H02K 15/024
  See application file for complete search history.

(56) References Cited

U.S. PATENT DOCUMENTS

| | | | | |
|---|---|---|---|---|
| 8,671,559 B2* | 3/2014 | Kleber | ............... | H02K 15/0081 29/564.1 |
| 2010/0326962 A1* | 12/2010 | Calla | .................... | B23K 9/0956 219/76.14 |
| 2012/0274162 A1* | 11/2012 | Kleber | ............... | H02K 15/0081 310/71 |

(Continued)

FOREIGN PATENT DOCUMENTS

JP 2014-238387 12/2014

*Primary Examiner* — Roy M Punnoose
(74) *Attorney, Agent, or Firm* — Amin, Turocy & Watson, LLP (57) ABSTRACT

The present invention relates to a welded section examining device. In order to examine whether welding is good or bad of a welded section joining tip portions of electrical conductors projecting from slots of a stator core, a welded section examining device includes a camera, a discriminating unit, a wavelength-converting sheet, and a masking member. The camera images the welded section. The discriminating unit performs discrimination of whether welding is good or bad based on an outline of the welded section recognized from an image of the welded section imaged by the camera. The wavelength-converting sheet irradiates the welded section with a light, from a rear surface side of an imaging target surface. The masking member is interposed between the wavelength-converting sheet and the rear surface of the welded section, such that the outline of the welded section is imaged in the camera in an emphasized state.

9 Claims, 8 Drawing Sheets

(56) References Cited

U.S. PATENT DOCUMENTS

| | | | | |
|---|---|---|---|---|
| 2013/0075371 A1* | 3/2013 | De Souza | ............ | G01N 25/72 |
| | | | | 219/109 |
| 2015/0202708 A1* | 7/2015 | Aoki | ............ | B23K 31/125 |
| | | | | 348/90 |
| 2015/0328721 A1* | 11/2015 | Abraham | ............ | B23K 31/125 |
| | | | | 416/201 R |
| 2018/0149621 A1* | 5/2018 | Chandelle | ............ | G01N 29/043 |

* cited by examiner

WELDED SECTION EXAMINING DEVICE

CROSS-REFERENCE TO RELATED APPLICATION

This application is based upon and claims the benefit of priority from Japanese Patent Application No. 2018-002220 filed on Jan. 10, 2018, the contents of which are incorporated herein by reference.

BACKGROUND OF THE INVENTION

Field of the Invention

The present invention relates to a welded section examining device that examines whether welding is good or bad of a welded section joining tip portions of legs of a plurality of electrical conductors projecting from slots of a stator core.

Description of the Related Art

A cylindrically shaped stator core included in a rotary electrical machine such as a motor or generator, has provided thereto, at intervals in a circumferential direction, a plurality of slots that penetrate the stator core in an axial direction. Each of the slots has inserted therein legs of a plurality of electrical conductors that are arranged in line in a radial direction of the stator core. A tip portion projecting from the slot of each of the legs is joined, by welding, to a tip portion of another leg projecting from another slot. Substantially spherically shaped welded sections are respectively formed at welding places of these tip portions.

For example, Japanese Laid-Open Patent Publication No. 2014-238387 proposes an examining device that examines whether welding is good or bad of the above-described welded section. This examining device includes: an imaging means that images the welded section; a light source that irradiates with light an imaging target surface facing the imaging means of the welded section; and a calculating section that extracts an outline of the welded section from an image acquired by the imaging means and thereby discriminates whether welding is good or bad of the welded section.

SUMMARY OF THE INVENTION

In the examining device where, as described above, an irradiating direction of the light source and an imaging direction of the imaging means are the same and therefore there is a risk that, due to a light of the light source being projected onto the imaging target surface of the welded section, and so on, at a time of imaging by the imaging means, precision of examining whether welding is good or bad will fall, or a configuration for examining whether welding is good or bad will become complicated.

A main object of the present invention is to provide a welded section examining device capable of easily and highly precisely examining whether welding is good or bad of a welded section.

According to an embodiment of the present invention, there is provided a welded section examining device that examines whether welding is good or bad of a welded section that joins a tip portion projecting from a slot of a plurality of slots provided at intervals in a circumferential direction of a stator core and a tip portion projecting from another slot of the plurality of slots, of legs of a plurality of electrical conductors that have been inserted, arranged in line in a radial direction of the stator core, in each of the plurality of slots, the device including: an imaging unit that images the welded section; a discriminating unit that performs discrimination of whether welding is good or bad based on an outline of the welded section recognized from an image obtained by the imaging unit; a projecting unit that irradiates the welded section with a light, from a rear surface side of an imaging target surface facing an imaging unit side of the welded section; and an outline emphasizing unit that is interposed between the projecting unit and the rear surface of the welded section, such that the outline of the welded section is imaged in the imaging unit in an emphasized state.

In this welded section examining device, the projecting unit causes the welded section to be irradiated with the light, from the rear surface side of its imaging target surface. Therefore, the imaging unit performs imaging in a state of the welded section being irradiated with a light representing a backlight for the imaging unit. This makes it possible to obtain a silhouette image of the welded section in which, for example, a background of the welded section is configured as a bright region and the welded section blocking an irradiation light is configured as a dark region.

In the silhouette image obtained as described above, the outline emphasizing unit causes the outline of the welded section to be emphasized. As a result, a precise outline of the welded section can be easily recognized by the discriminating unit, hence it becomes possible to easily and highly precisely examine whether welding is good or bad of the welded section based on the outline.

The above-described welded section examining device may be configured such that the outline emphasizing unit, by being disposed on the rear surface side of at least part of the welded section and partially blocking an irradiation light from the projecting unit, forms a background having a color difference with a light that advances in a direction inclined with respect to an imaging direction of the imaging unit to irradiate the outline of the welded section.

In this case, the outline of the welded section is irradiated by the light (hereafter, also called an inclined light) advancing in the direction inclined with respect to the imaging direction, hence, even in such a case as when the bright region occurs in the outline of the welded section that originally would be a dark region, the outline emphasizing unit blocking the irradiation light on the rear surface side of the bright region makes it possible to form a background of a color different from that of the bright region. In other words, the outline of the welded section can be emphasized by a simple configuration of partially blocking the irradiation light.

The above-described welded section examining device may be configured such that the outline emphasizing unit includes a blocking section disposed so as to block a light that advances in a direction inclined with respect to an imaging direction of the imaging unit toward the outline of the welded section, of an irradiation light from the projecting unit and transmit a light that advances along the imaging direction of the imaging unit, of the irradiation light from the projecting unit.

In this case, the outline of the welded section being irradiated by the inclined light can in fact be suppressed by the blocking section, hence it can be suppressed that the outline of the welded section blurs. That is, the outline of the welded section can be emphasized by the blocking section. Therefore, in the discriminating unit, the outline of the welded section can be accurately and easily recognized, based on an image in which the outline has been clearly indicated. As a result, it becomes possible to even more easily and highly precisely examine whether welding is good or bad of the welded section.

In the above-described welded section examining device, the outline emphasizing unit preferably includes: a plurality of the blocking sections that are louver-like and configured from a light-absorbing material; and a film configured from a light-transmitting material that holds the plurality of blocking sections in a state of being arranged in line with each other at intervals. In this case, it is possible for the light advancing along the imaging direction, of the irradiation light from the projecting unit to be transmitted through a space between blocking sections and through the film. On the other hand, the inclined light advancing toward the blocking section is absorbed by the blocking section, hence it is suppressed that the welded section is irradiated by the inclined light. Therefore, this outline emphasizing unit makes it possible for the outline of the welded section to be effectively emphasized by a simple configuration made up of the louver-like blocking sections and the film.

In the above-described welded section examining device, the projecting unit preferably irradiates from the rear surface side of the welded section with a reflected light of a light irradiated from the light source. In this case, since the projecting unit can be given a simple configuration of reflecting the light from the light source, a lowering of costs of the welded section examining device can be achieved.

In the above-described welded section examining device, the projecting unit preferably irradiates the welded section with a reflected light of a wavelength different from that of the light irradiated from the light source. In this case, the reflected light with which the welded section is irradiated and the light of the light source have different wavelengths, so it becomes possible that, even if the light of the light source has entered the imaging unit, the light of the light source and the reflected light are discriminated and thereby recognized in the image acquired by the imaging unit. As a result, the outline of the welded section can be accurately recognized, whereby it can be highly precisely examined whether welding is good or bad.

The above-described welded section examining device preferably further includes a light-absorbing unit that is provided between the welded section and the imaging unit and absorbs a light of the same wavelength as the light irradiated from the light source. In this case, of the reflected light from the projecting unit and the light of the light source that are heading for the imaging unit, only the light of the light source is absorbed by the light-absorbing unit before entering the imaging unit. Therefore, it can be avoided that the light of the light source lowers a contrast of the outline of the welded section in the image acquired by the imaging unit. As a result, it becomes possible to obtain an image in which the outline of the welded section is indicated even more clearly, hence examination of whether welding is good or bad can be performed easily and highly precisely.

In the above-described welded section examining device, the projecting unit may be a light source disposed on the rear surface side of the welded section. In this case, the projecting unit itself emits light, so to the extent that another light source can be rendered unnecessary; it is possible to reduce the number of components of the welded section examining device.

In the above-described welded section examining device, it is preferable that the imaging unit simultaneously images a plurality of the welded sections aligned at intervals in the radial direction of the stator core, the discriminating unit performs discrimination of whether welding is good or bad of each of the plurality of welded sections, the projecting unit irradiates the plurality of welded sections with the light, from the rear surface side, and the outline emphasizing unit is provided such that the outlines of the plurality of welded sections are imaged in the imaging unit in a state of each having been emphasized. In this case, the welded section examining device makes it possible to efficiently examine whether welding is good or bad of a plurality of welded sections.

The above and other objects, features, and advantages of the present invention will become more apparent from the following description when taken in conjunction with the accompanying drawings, in which preferred embodiments of the present invention are shown by way of illustrative example.

DESCRIPTION OF THE PREFERRED EMBODIMENTS

Preferred embodiments of a welded section examining device according to the present invention will be presented and described in detail with reference to the accompanying drawings. Note that in the drawings below, configuring elements displaying the same or similar functions and advantages will be assigned with the same reference symbols, and repeated descriptions thereof will sometimes be omitted.

Figure 1:
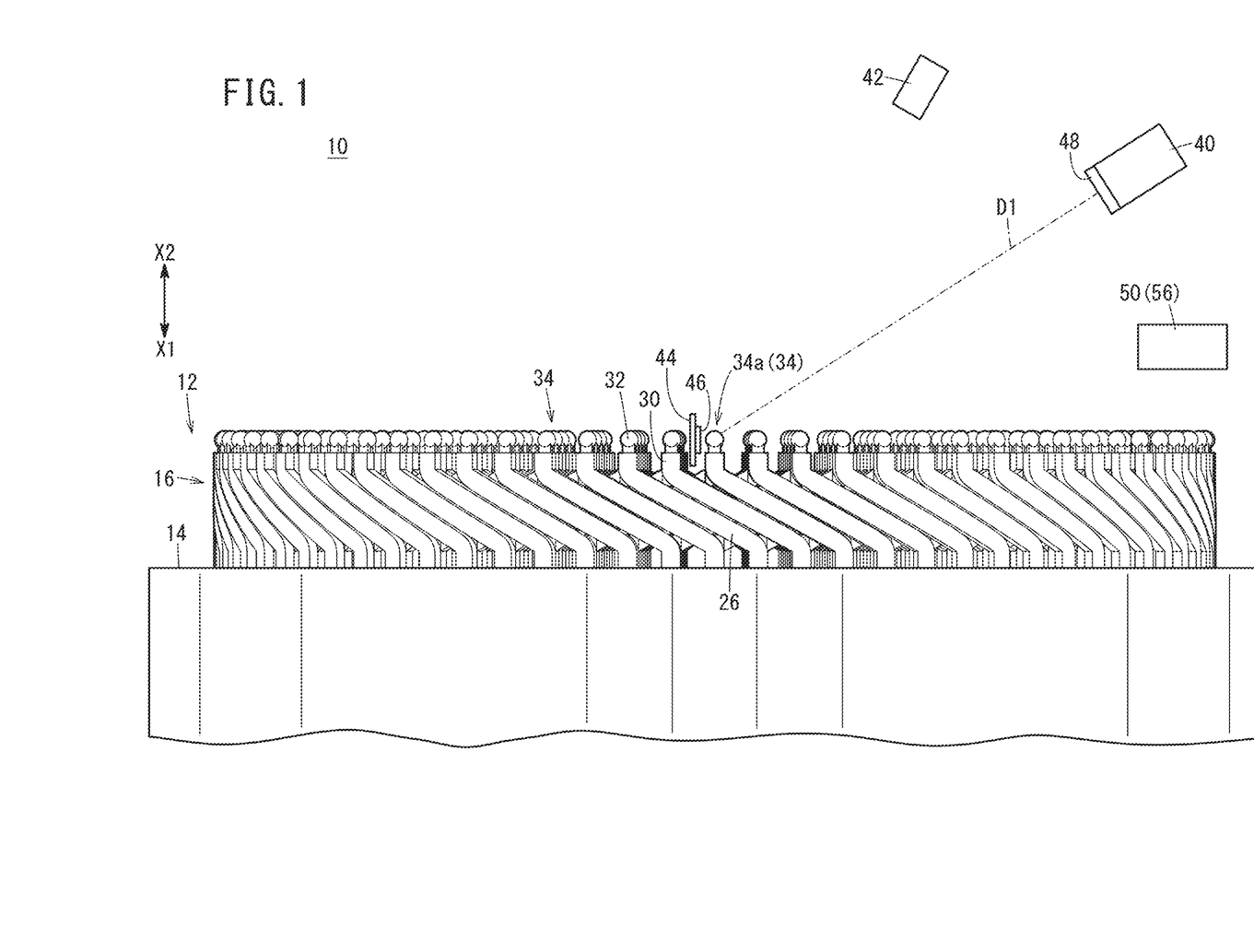
FIG. 1 is a schematic side view of a welded section examining device according to a first embodiment.
Figure 2:
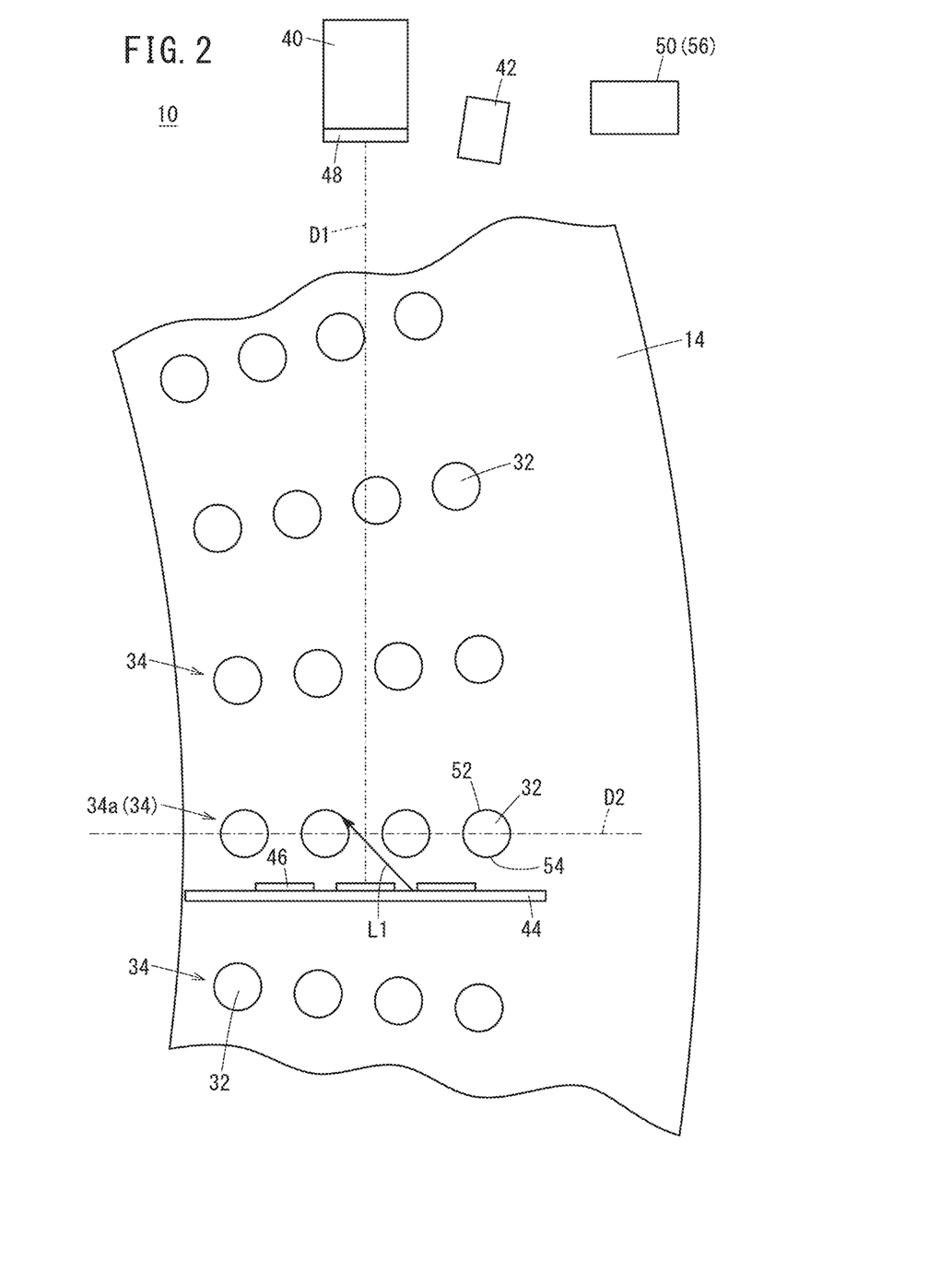
FIG. 2 is a schematic plan view of essential parts of the welded section examining device of FIG. 1.
Figure 3:
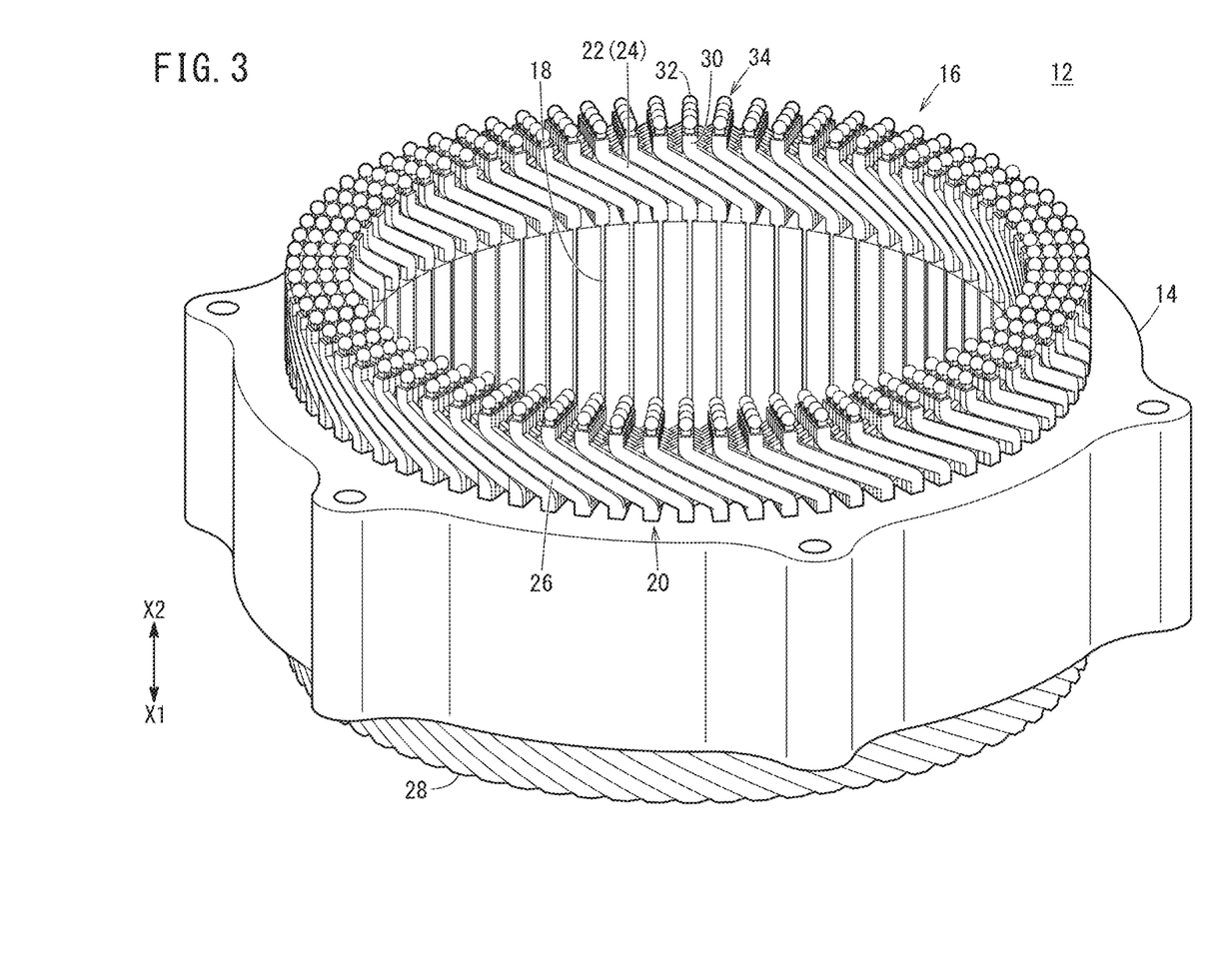
FIG. 3 is a schematic perspective view of a stator applied to the welded section examining device of FIG. 1.

As shown in FIGS. 1 and 2, a welded section examining device 10 according to a first embodiment can be applied to a stator 12 shown in FIG. 3, for example. The stator 12 includes: a stator core 14 of substantially cylindrical shape; and a coil 16. Note that hereafter, each of configuring elements of the stator 12 will be described with reference to an axial direction (a direction of arrows X1, X2 in FIG. 3), a radial direction, and a circumferential direction of the stator core 14.

A plurality of slots 18 that penetrate the stator core 14 in the axial direction are provided at intervals in the circumferential direction, in the stator core 14. The coil 16 is configured from a plurality of segment groups 20. Each of the segment groups 20 is configured by arranging in line in the radial direction a certain number of (in the present embodiment, four) segments 24 that are each formed by bending an electrical conductor 22 of rectangular shaped cross section, for example. Each of the segments 24 includes: a pair of legs 26 that extend in the axial direction;

and a coupling section 28 that couples these legs 26 on one end side (a side of arrow X1 in FIG. 3) in the axial direction.

The pairs of legs 26 of the plurality of segments 24 configuring each of the segment groups 20 are respectively inserted in slots 18 that differ from each other. A tip portion 30 of the leg 26 projecting from one of the slots 18 is joined by welding to another tip portion 30 projecting from a different one of the slots 18, and, at places of welding with each other, welded sections 32 of substantially spherical shape are respectively formed. In the present embodiment, four welded sections 32 form a lined-up group 34 in which they are arranged in line at intervals in the radial direction, and the same number of these lined-up groups 34 as there are slots 18, are provided at intervals in the circumferential direction.

The welded section examining device 10 according to the present embodiment examines whether welding is good or bad of the above-described welded section 32. As shown in FIGS. 1 and 2, the welded section examining device 10 mainly includes: a camera 40 (an imaging unit); a light source 42; a wavelength-converting sheet 44 (a projecting unit); a masking member 46 (an outline emphasizing unit); a light-absorbing unit 48; and a control section 50. Note that each of configuring elements of the welded section examining device 10 is, for example, held so as to be in a certain disposition with respect to the stator 12, by an unillustrated holding mechanism, or the like.

Figure 4:
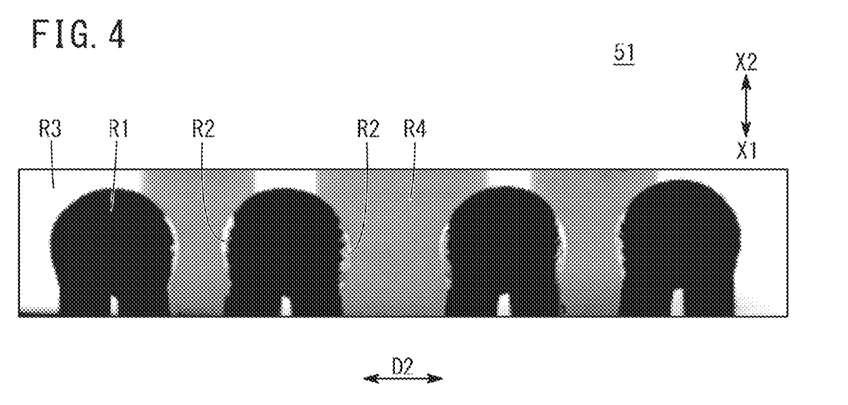
FIG. 4 is a sample of an acquired image in the welded section examining device of FIG. 1.

The camera 40 is configured from the likes of a CCD camera, and images the lined-up group 34 (hereafter, also called a target lined-up group 34a) of the welded sections 32 as an examination target, thereby acquiring an image 51 shown in FIG. 4, for example. In the present embodiment, a surface facing a camera 40 side of each of the welded sections 32 configuring the target lined-up group 34a represents an imaging target surface 52 (refer to FIG. 2). The camera 40 has its positional relationship with the stator 12 adjusted such that imaging of the target lined-up group 34a will be in an imaging direction D1 not hindered by another lined-up group 34. For example, the imaging direction D1 can be set so as to extend, at an angle with respect to the axial direction of the stator core 14, from the camera 40 disposed more to a different end side (a side of arrow X2) than the welded sections 32 are in the axial direction, toward the target lined-up group 34a as in FIG. 1, and so as to substantially be orthogonal to a lining-up direction D2 of the welded sections 32 of the target lined-up group 34a as in FIG. 2.

The light source 42 is configured from the likes of a blue LED, for example, and irradiates the wavelength-converting sheet 44 with a blue light. The wavelength-converting sheet 44 is disposed on a rear surface 54 (refer to FIG. 2) side of the imaging target surface 52 of the target lined-up group 34a, and, by reflecting the blue light irradiated from the light source 42 converting it to, for example, an orange light as its complementary color, irradiates the target lined-up group 34a with this reflected light, from its rear surface 54 side. In the present embodiment, the wavelength-converting sheet 44 is configured in a rectangular shape having the lining-up direction D2 of the target lined-up group 34a as its long side. Note that hereafter, more to a camera 40 side than the imaging target surface 52 will also be called a front side, and more to a wavelength-converting sheet 44 side than the imaging target surface 52 will also be called a rear side.

The masking member 46 is disposed between the rear surface 54 of at least part of the welded section 32 in the target lined-up group 34a and the wavelength-converting sheet 44, and is configured from a material that blocks the reflected light from the wavelength-converting sheet 44. In the present embodiment, a total of three masking members 46 are respectively arranged on the rear side between adjacent welded sections 32 of the target lined-up group 34a, as shown in FIG. 2. Note that the masking member 46 may be adhered to a surface on a side facing the welded section 32 of the wavelength-converting sheet 44.

The light-absorbing unit 48 is configured from the likes of a cut filter that absorbs a light of the same wavelength as the blue light irradiated from the light source 42, and, for example, by being disposed so as to cover a lens of the camera 40, suppresses that the blue light enters the camera 40.

The control section 50 is configured as a computer including the likes of an unillustrated CPU or memory. A control program stored in the memory is read and executed by the CPU, whereby the control program can cause hardware such as the CPU to function as a discriminating unit 56. The discriminating unit 56 recognizes an outline of each of the welded sections 32 of the target lined-up group 34a from the image transmitted from the camera 40, and performs discrimination of whether welding is good or bad based on the outline.

Figure 5A:
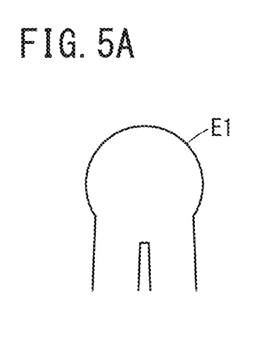
FIG. 5A is an explanatory diagram for explaining one example of an outline of a welded section discriminated as a pass.
Figure 5B:
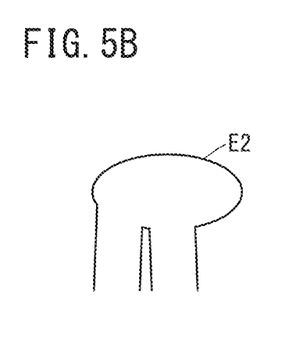
FIG. 5B is an explanatory diagram for explaining one example of an outline of a welded section discriminated as a fail.

The following may be cited as a standard for discriminating whether welding is good or bad, namely, for example, that a pass is assumed in the case where a shape of the recognized outline has an arc section of substantially a perfectly circular shape, as in an outline E1 shown in FIG. 5A, and that a fail is assumed in the case where the shape of the recognized outline does not have an arc section of substantially a perfectly circular shape, as in an outline E2 shown in FIG. 5B. However, the standard is not particularly limited to these, and discrimination of whether welding is good or bad can be performed using a variety of detection data capable of being obtained from the recognized outline of the welded section 32, such as a dimension of the welded section 32 or a positional relationship of the welded section 32 and the leg 26, for example.

The welded section examining device 10 according to the first embodiment is basically configured as above. Next, a method of examining whether welding is good or bad of the welded section 32 using this welded section examining device 10 will be described.

First, the stator 12 is set in the welded section examining device 10 such that the target lined-up group 34a adopted as the examination target selected from the plurality of lined-up groups 34 provided in the circumferential direction of the stator core 14 will be in the above-described positional relationship with respect to each of the configuring elements of the welded section examining device 10. This setting may be performed by, for example, using the likes of an unillustrated rotary mechanism or raising-and-lowering mechanism to move the stator 12 relatively to the camera 40 or wavelength-converting sheet 44, and so on, held in advance in a certain position by the likes of the above-described holding mechanism.

Next, the wavelength-converting sheet 44 is irradiated with the blue light from the light source 42. As a result, the wavelength-converting sheet 44 irradiates the target lined-up group 34a with the orange reflected light, from a rear surface 54 side of the target lined-up group 34a. Next, the target lined-up group 34a is imaged by the camera 40, and, for example, the image 51 shown in FIG. 4 is acquired. In this image 51, the welded section 32 and part of the tip portion 30 that block an irradiation light from the wavelength-converting sheet 44, are shown by a dark region R1. By the outline of the welded section 32 being irradiated by the inclined light L1 that advances in a direction inclined to the imaging direction D1 as shown in FIG. 2, a bright region R2 is formed in this dark region R1. Moreover, in the image 51, a portion not provided with the masking member 46 of the wavelength-converting sheet 44 is shown by a bright region R3, and a portion provided with the masking member 46 of the wavelength-converting sheet 44 is shown by an intermediate region R4 having a color difference with the bright region R2.

That is, in the image 51, due to the outline of the welded section 32 being irradiated by the inclined light L1, the bright region R2 occurs in the outline of the welded section 32 that originally would be a dark region, for example. Even in such a case, due to the masking member 46 that blocks the irradiation light on the rear side of the welded section 32, a background of the bright region R2 can be configured as the intermediate region R4. As a result, in the image 51, the outline of the welded section 32 of the target lined-up group 34a can be emphasized more compared to in an image 58 (refer to FIG. 6) according to a comparative example obtained by, for example, imaging the target lined-up group 34a without the masking member 46 being provided.

Figure 6:
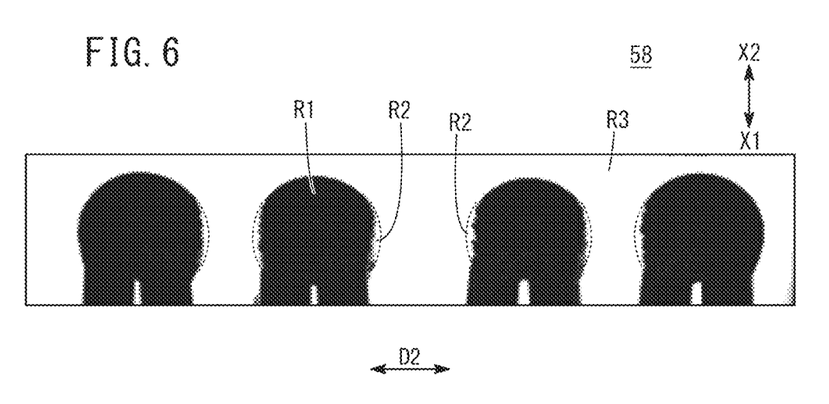
FIG. 6 is an image according to a comparative example.

Note that in the image 58, the bright region R2 generated by the inclined light L1 is blurring the precise outline of the welded section 32 shown by the broken line in FIG. 6. Therefore, it is difficult to recognize the precise outline of the welded section 32 from the image 58.

Next, the outline of each of the welded sections 32 of the target lined-up group 34a is recognized from the image 51, by the discriminating unit 56, and it is discriminated whether welding is good or bad, based on this outline. As a result, examination of whether welding is good or bad for each of the welded sections 32 of the target lined-up group 34a finishes.

In the case of examining whether welding is good or bad for the welded sections 32 of another lined-up group 34 provided in the stator 12 too, all that is required is to select a new target lined-up group 34a to be adopted as the examination target from the other lined-up groups 34, and perform similar steps to those described above.

As stated above, in this welded section examining device 10, the light is irradiated from the rear surface 54 side of the welded section 32 by the wavelength-converting sheet 44. Therefore, the camera 40 performs imaging in a state where the welded section 32 has been irradiated with a light representing a backlight for the camera 40. As a result, the image 51 of the silhouette of the welded section 32 can be obtained.

In this image 51, contrary to in an image (not illustrated) obtained by, for example, imaging the welded section 32 from the same direction as the irradiating direction of the light, it can be avoided that the irradiation light, and so on, is projected onto the imaging target surface 52 of the welded section 32. Moreover, in the image 51, as described above, the outline of the welded section 32 is emphasized by the masking member 46. As a result, the precise outline of the welded section 32 can be easily recognized by the discriminating unit 56, hence it becomes possible to easily and highly precisely discriminate whether welding is good or bad of the welded section 32, based on the outline.

As described above, in the welded section examining device 10, a configuration was adopted to include the light source 42 and to irradiate from the rear surface 54 side of the target lined-up group 34a with the reflected light being an emitted light of the light source 42 that has been reflected by the wavelength-converting sheet 44. In this case, the configuration for irradiating the welded section 32 with the light can be simplified, hence a lowering of costs of the welded section examining device 10 can be achieved.

As described above, in the welded section examining device 10, a configuration was adopted to irradiate the target lined-up group 34a with the reflected light being the blue light emitted from the light source 42 that has been converted to the orange light by the wavelength-converting sheet 44. In this case, since the reflected light irradiating the welded section 32 and the light of the light source 42 have different wavelengths, then, even if the light of the light source 42 has entered the camera 40, it is possible for the light of the light source 42 and the reflected light to be distinguished and recognized in the image 51. As a result, the outline of the welded section 32 can be accurately recognized, and it can be highly precisely examined whether welding is good or bad.

As described above, the welded section examining device 10 includes the light-absorbing unit 48. Therefore, of the reflected light from the wavelength-converting sheet 44 and the light of the light source 42 that are heading for the camera 40, only the light of the light source 42 is absorbed by the light-absorbing unit 48 before entering the camera 40. Therefore, it can be avoided that the light of the light source 42 lowers a contrast of the outline of the welded section 32 in the image 51. As a result, it becomes possible to acquire the image 51 in which the outline of the welded section 32 is indicated even more clearly, hence examination of whether welding is good or bad can be performed easily and highly precisely.

Next, a welded section examining device 60 according to a second embodiment will be described with reference to FIGS. 7 and 8. The welded section examining device 60 is configured similarly to the welded section examining device 10 according to the first embodiment, apart from including a light-transmitting direction control sheet 62 (an outline emphasizing unit) instead of the above-described masking member 46.

Figure 7:
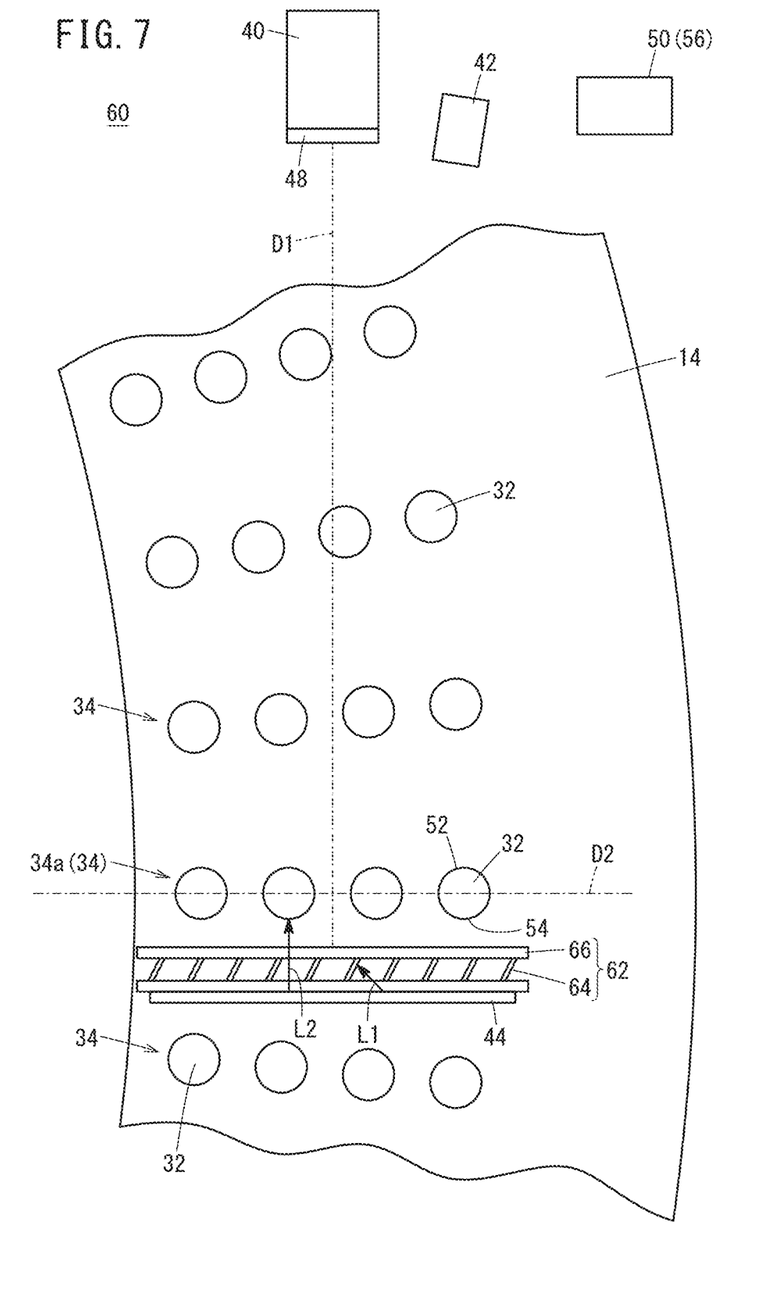
FIG. 7 is a schematic plan view of essential parts of a welded section examining device according to a second embodiment.

As shown in FIG. 7, the light-transmitting direction control sheet 62 is disposed between the wavelength-converting sheet 44 and the target lined-up group 34a. In the present embodiment, the light-transmitting direction control sheet 62 is of a rectangular shape having the lining-up direction D2 of the target lined-up group 34a as its long side, and has its dimensions set slightly larger than those of the wavelength-converting sheet 44. Note that the light-transmitting direction control sheet 62 may be adhered to the surface on the side facing the welded section 32 of the wavelength-converting sheet 44.

The light-transmitting direction control sheet 62 includes: a plurality of blocking sections 64 that are louver-like and configured from a light-absorbing material; and a pair of films 66 configured from a light-transmitting material that hold the plurality of blocking sections 64. The pair of films 66 have each of their surface directions lying along a surface direction of the wavelength-converting sheet 44, and are disposed facing each other at an interval in a direction substantially orthogonal to the surface direction. The plurality of blocking sections 64 are positioned and fixed between these pair of films 66 in a state of being arranged at intervals in the lining-up direction D2. Note that as shown in FIG. 7, each of the plurality of blocking sections 64 may have its surface direction disposed so as to incline with respect to the direction substantially orthogonal to the surface direction of the film 66.

In this light-transmitting direction control sheet 62, the inclined light L1 heading for the outline of the welded section 32, of the reflected light from the wavelength-converting sheet 44, is blocked by the blocking section 64, whereby it can be suppressed that the inclined light L1 is irradiated to a target lined-up group 34a side. On the other hand, the light L2 advancing along the imaging direction D1, of the reflected light from the wavelength-converting sheet 44, can be transmitted to the target lined-up group 34a side, via a space between blocking sections 64 and via the film 66.

Figure 8:
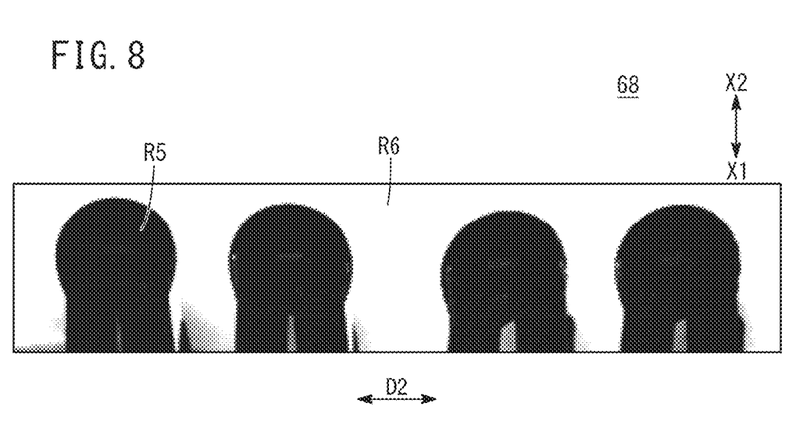
FIG. 8 is a sample of an acquired image in the welded section examining device of FIG. 7.

In the welded section examining device 60 including this light-transmitting direction control sheet 62, the target lined-up group 34a is imaged by the camera 40, whereby, for example, an image 68 shown in FIG. 8 can be acquired. In this image 68, the welded section 32 that blocks the irradiation light from the wavelength-converting sheet 44 is shown by a dark region R5, and the wavelength-converting sheet 44 mediated by the light-transmitting direction control sheet 62 is shown by a bright region R6.

That is, in the image 68, the outline of the welded section 32 being irradiated by the inclined light L1 can in fact be suppressed by the blocking section 64, hence it can be avoided that a bright region occurs in a portion indicating the outline of the welded section 32, of the dark region R5. Thus, the precise outline of the welded section 32 of the target lined-up group 34a is more clearly indicated, compared to, for example, in the image 58 according to the comparative example shown in FIG. 6, so the image 68 having that outline emphasized is transmitted to the discriminating unit 56 from the camera 40. As a result, it becomes possible for the outline of the welded section 32 to be accurately and easily recognized by the discriminating unit 56, so it can be even more easily and highly precisely examined whether welding is good or bad of the welded section 32.

The present invention is not particularly limited to the above-described embodiments, and may be variously modified in a range not departing from the spirit of the present invention.

For example, the welded section examining devices 10, 60 may be configured to include an unillustrated light source (a projecting unit) disposed on the rear surface 54 side of the welded section 32 of the target lined-up group 34a, instead of the light source 42 and the wavelength-converting sheet 44, in order to achieve a reduction in the number of components, and so on. The light source in this case is preferably a sheet-like organic EL, or the like, from a viewpoint of efficiently irradiating each of the welded sections 32 of the target lined-up group 34a with the light.

In the above-described welded section examining devices 10, 60, a configuration was adopted in which the images 51, 68 having the four welded sections 32 of the target lined-up group 34a simultaneously imaged by the camera 40 were respectively acquired, whereby it was efficiently examined whether welding was good or bad of a plurality of the welded sections 32 provided in the stator 12. However, the present invention is not particularly limited to this, and examination of whether welding is good or bad may be performed by imaging the welded sections 32 one at a time by the camera 40, or examination of whether welding is good or bad may be performed by simultaneously imaging a plurality of other than four of the welded sections 32 by the camera 40.

In the above-described welded section examining devices 10, 60, the shape of the wavelength-converting sheet 44 was configured in a rectangular shape having the lining-up direction D2 as its long side. In this case, an area of a portion separated in the lining-up direction D2 from each of the welded sections 32 of the target lined-up group 34a, of the wavelength-converting sheet 44 will be larger compared to an area of a portion separated in the axial direction from each of the welded sections 32 of the target lined-up group 34a, of the wavelength-converting sheet 44. Therefore, a proportion of the inclined light L1 heading for the welded section 32 from the portion separated in the lining-up direction D2 from the welded section 32, of the wavelength-converting sheet 44 will be larger compared to that from the portion separated in the axial direction from the welded section 32, of the wavelength-converting sheet 44. In other words, the proportion of the inclined light L1 heading for portions on both end sides in the lining-up direction D2, of the outline of the welded section 32 will be larger compared to that heading for portions on both end sides in the axial direction, of the outline of the welded section 32.

Furthermore, in the above-described embodiments, a length of the long side of the wavelength-converting sheet 44 is of a degree slightly longer than a length in the lining-up direction D2 of the target lined-up group 34a, hence a proportion of the inclined light L1 heading for the outline of the welded sections 32 closely adjacent to both end sections of the long side of the wavelength-converting sheet 44 will be comparatively small.

Therefore, in the welded section examining device 10, a configuration was adopted in which the masking members 46 were respectively disposed on the rear side between adjacent welded sections 32 of the target lined-up group 34a, and a portion easily irradiated by the inclined light L1, of the outline of the welded section 32 was emphasized.

On the other hand, in the welded section examining device 60, a configuration was adopted in which the plurality of blocking sections 64 were arranged at intervals in the lining-up direction D2, whereby the inclined light L1 heading for the welded section 32 from the portion separated in the lining-up direction D2 from the welded section 32, of the wavelength-converting sheet 44 was effectively blocked.

However, the shape of the wavelength-converting sheet 44 is not particularly limited to the above-described rectangular shape. For example, when a ratio of length in the axial direction of the wavelength-converting sheet 44 to length in the axial direction of the welded section 32 gets large, the inclined light (not illustrated) heading for the portions on both sides in the axial direction, of the outline of the welded section 32 also tends to increase. Moreover, when a ratio of length of the long side of the wavelength-converting sheet 44 to length in the lining-up direction D2 of the target lined-up group 34a gets large, the inclined light L1 heading for the outline of the welded sections 32 closely adjacent to both end sections of the long side of the wavelength-converting sheet 44 also sometimes increases.

In these cases, in the welded section examining device 10, the masking member 46 may be disposed on the rear side of both end sides in the axial direction of the target lined-up group 34a or also on the rear side of the outline of the welded sections 32 closely adjacent to both end sections of the long side of the wavelength-converting sheet 44.

Similarly, in the welded section examining device 60, a configuration may be adopted in which the inclined light heading for the welded section 32 from both the portion separated in the lining-up direction D2 from the welded section 32 and the portion separated in the axial direction from the welded section 32, of the wavelength-converting sheet 44, can be blocked by the blocking section 64. The following may be cited as an example of such a light-transmitting direction control sheet 62, namely, configuring the blocking section 64 as a laminated structure (not illustrated) of a first layer arranged at intervals in the lining-up direction D2 and a second layer arranged at intervals in the axial direction.

Although in the above-described welded section examining device 60, a configuration was adopted in which the light-transmitting direction control sheet 62 included the plurality of blocking sections 64 that were louver-like, and the pair of films 66 sandwiching these blocking sections 64, the present invention is not particularly limited to this. There may be employed as the light-transmitting direction control sheet 62 a well-known one having a configuration that selectively transmits only a light of a certain orientation, of a light entering the light-transmitting direction control sheet 62.

The welded section examining devices 10, 60 may include a reflecting member (not illustrated) that reflects a light of the same wavelength as the light of the light source 42, instead of the wavelength-converting sheet 44, and may omit the light-absorbing unit 48. Moreover, the emitted light of the light source 42 is not limited to being the blue light.

What is claimed is:

1. A welded section examining device that examines whether welding is good or bad of a welded section that joins a tip portion projecting from a slot of a plurality of slots provided at intervals in a circumferential direction of a stator core and a tip portion projecting from another slot of the plurality of slots, of legs of a plurality of electrical conductors that have been inserted, arranged in line in a radial direction of the stator core, in each of the plurality of slots, the device comprising:
    an imaging unit that images the welded section;
    a discriminating unit that performs discrimination of whether welding is good or bad based on an outline of the welded section recognized from an image obtained by the imaging unit;
    a projecting unit that irradiates the welded section with a light, from a rear surface side of an imaging target surface facing an imaging unit side of the welded section; and
    an outline emphasizing unit that is interposed between the projecting unit and the rear surface of the welded section, such that the outline of the welded section is imaged in the imaging unit in an emphasized state.

2. The welded section examining device according to claim 1, wherein
    the outline emphasizing unit, by being disposed on the rear surface side of at least part of the welded section and partially blocking an irradiation light from the projecting unit, forms a background having a color difference with a light that advances in a direction inclined with respect to an imaging direction of the imaging unit to irradiate the outline of the welded section.

3. The welded section examining device according to claim 1, wherein
    the outline emphasizing unit includes a blocking section disposed so as to block a light that advances in a direction inclined with respect to an imaging direction of the imaging unit toward the outline of the welded section, of an irradiation light from the projecting unit and transmit a light that advances along the imaging direction of the imaging unit, of the irradiation light from the projecting unit.

4. The welded section examining device according to claim 3, wherein
    the outline emphasizing unit includes:
    a plurality of the blocking sections that are louver-like and configured from a light-absorbing material; and
    a film configured from a light-transmitting material that holds the plurality of blocking sections in a state of being arranged in line with each other at intervals.

5. The welded section examining device according to claim 1, wherein
    the projecting unit irradiates from the rear surface side of the welded section with a reflected light of a light irradiated from the light source.

6. The welded section examining device according to claim 5, wherein
    the projecting unit irradiates the welded section with a reflected light of a wavelength different from that of the light irradiated from the light source.

7. The welded section examining device according to claim 6, further comprising
    a light-absorbing unit that is provided between the welded section and the imaging unit and absorbs a light of the same wavelength as the light irradiated from the light source.

8. The welded section examining device according to claim 1, wherein
    the projecting unit is a light source disposed on the rear surface side of the welded section.

9. The welded section examining device according to claim 1, wherein
    the imaging unit simultaneously images a plurality of the welded sections aligned at intervals in the radial direction of the stator core,
    the discriminating unit performs discrimination of whether welding is good or bad of each of the plurality of welded sections,
    the projecting unit irradiates the plurality of welded sections with the light, from the rear surface side, and
    the outline emphasizing unit is provided such that the outlines of the plurality of welded sections are imaged in the imaging unit in a state of each having been emphasized.

* * * * *